US012648746B2

(12) United States Patent
Nagel et al.

(10) Patent No.: US 12,648,746 B2
(45) Date of Patent: Jun. 9, 2026

(54) CLEANING DEVICE FOR A TOMOGRAPHY DEVICE HAVING AN EXAMINATION TUNNEL AND TOMOGRAPHY DEVICE

(71) Applicant: RADIOLOGY INNOVATIONS NB20C GMBH, Bubenreuth (DE)

(72) Inventors: Armin Michael Nagel, Bubenreuth (DE); Sebastian Bickelhaupt, Erlangen (DE)

(73) Assignee: Radiology Innovations NB20C GmbH, Bubenreuth (DE)

( * ) Notice: Subject to any disclaimer, the term of this patent is extended or adjusted under 35 U.S.C. 154(b) by 596 days.

(21) Appl. No.: 18/088,915

(22) Filed: Dec. 27, 2022

(65) Prior Publication Data

US 2023/0136855 A1      May 4, 2023

Related U.S. Application Data

(63) Continuation of application No. PCT/EP2021/064387, filed on May 28, 2021.

(30) Foreign Application Priority Data

Jun. 27, 2020      (DE) ...................... 10 2020 207 984.6

(51) Int. Cl.
*A61B 6/00*            (2024.01)
*A61L 2/10*            (2006.01)
(Continued)

(52) U.S. Cl.
CPC .............. *A61B 6/4423* (2013.01); *A61L 2/10* (2013.01); *A61L 2/18* (2013.01); *A61L 2103/05* (2026.01);
(Continued)

(58) Field of Classification Search
CPC ..... A61B 6/4423; A61B 6/035; A61L 2/0047; A61L 2/0088; A61L 2202/15; A61L 2202/24
See application file for complete search history.

(56) References Cited

U.S. PATENT DOCUMENTS 2,930,059 A * 3/1960 Frank ...................... B08B 9/045
                                                                 15/104.18
5,918,342 A      7/1999 Smith et al.
(Continued)

FOREIGN PATENT DOCUMENTS

CN          107582255 A      1/2018
CN          108028212 A      5/2018
(Continued)

OTHER PUBLICATIONS

Norman Butler et al: "Device f or MRI scanner intra-bore disinfection", Penn Center for Innovation, Empowering Ideas, Penn Center for Innovation, US Jun. 23, 2020 (Jun. 23, 2020), p. 1, XP009528630, Found on the Internet: URL:https://upenn. technologypublisher.com/ technology/40453, the whole document.

*Primary Examiner* — Regina M Yoo
(74) *Attorney, Agent, or Firm* — Laurence A. Greenberg; Werner H. Stemer; Ralph E. Locher

(57)        ABSTRACT
A cleaning device for a tomography device, in particular an MRT, has an examination tunnel. The cleaning device has a nozzle assembly for applying a liquid cleaning agent to a tunnel inner surface facing toward the tunnel axis, a mounting device, which is configured to mount the nozzle assembly on a structural unit of the tomography device parallel to the tunnel axis and displaceably along the examination tunnel, and a control unit, which is configured, in the intended cleaning operation, to specify the application of the cleaning agent in dependence on the movement of the nozzle assembly.

7 Claims, 2 Drawing Sheets

(51) Int. Cl.
  *A61L 2/18*        (2006.01)
  *A61L 103/05*        (2026.01)
  *A61L 103/15*        (2026.01)

(52) U.S. Cl.
  CPC ....... *A61L 2103/15* (2026.01); *A61L 2202/15*
                                              (2013.01)

(56)                    References Cited

U.S. PATENT DOCUMENTS

|  |  |  |  |  |
|---|---|---|---|---|
| 6,093,255 | A | 7/2000 | Smith et al. | |
| 10,475,672 | B2 | 11/2019 | Fehkuhrer | |
| 11,279,605 | B2 | 3/2022 | Soellner et al. | |
| 12,090,531 | B2 * | 9/2024 | Martinez | B08B 9/0808 |
| 2012/0195410 | A1 | 8/2012 | O'Connor et al. | |
| 2014/0336495 | A1 | 11/2014 | Bittner | |
| 2020/0238955 | A1 | 7/2020 | Walsøe et al. | |

FOREIGN PATENT DOCUMENTS

| | | |
|---|---|---|
| CN | 110997426 A | 4/2020 |
| CN | 111071511 A | 4/2020 |
| CN | 111249505 A | 6/2020 |
| CN | 111281409 A | 6/2020 |
| DE | 19523615 A1 | 1/1997 |
| DE | 10312048 A1 | 5/2004 |
| DE | 202013100769 U1 | 3/2013 |
| DE | 102013208340 A1 | 11/2014 |
| JP | 2006088002 A | 4/2006 |
| JP | 2006149560 A | 6/2006 |
| WO | 2010146482 A1 | 12/2010 |

* cited by examiner

CLEANING DEVICE FOR A TOMOGRAPHY DEVICE HAVING AN EXAMINATION TUNNEL AND TOMOGRAPHY DEVICE

CROSS-REFERENCE TO RELATED APPLICATION

This application is a continuation, under 35 U.S.C. § 120, of copending International Patent Application PCT/EP2021/064387, filed May 28, 2021, which designated the United States; this application also claims the priority, under 35 U.S.C. § 119, of German Patent Application DE 10 2020 207 984.6, filed Jun. 27, 2020; the prior applications are herewith incorporated by reference in their entireties.

FIELD AND BACKGROUND OF THE INVENTION

The invention relates to a cleaning device for a tomography device having an examination tunnel. Furthermore, the invention relates to such a tomography device.

Tomography devices are used, as the name already indicates, in particular for creating sectional images of an examination object, for example a patient. A variant for creating the sectional images is the use of x-ray radiation, for example in a computer tomography device (abbreviated: CT). A further variant is so-called magnetic resonance tomography (also called nuclear spin tomography), which is used in a magnetic resonance tomography device (abbreviated: MRT). In addition, combination devices are known, for example a positron emission MRT (abbreviated: PET-MRT), a PET-CT, and the like. Tomography devices typically have an examination tunnel into which the examination object is pushed. In a computer tomography device, this examination tunnel is formed by the so-called gantry, which in turn carries an x-ray radiation source mounted on a rotating ring and typically an x-ray detector opposite thereto. In a device based on magnetic resonance tomography (abbreviated: MR), the examination tunnel is formed by the annularly arranged magnetic coils.

In particular in the examination of patients, cleaning of the surfaces of the tomography devices is important to avoid smear infections when the surfaces are touched by the patients. Especially in MRTs, however, the examination tunnels (with regard to their diameter) are comparatively small-typically in the range around 60 to 70 cm—and often also comparatively elongated. Thus, in MR-based tomography devices (in particular for whole-body examination), tunnel lengths of greater than 1 m are typical, and lengths of greater than 1.6 to almost 3 m are also known. This tunnel length together with the comparatively small diameter is known to result in comparatively poor accessibility to the inside of the examination tunnel, the "tunnel inner surface".

In addition, modern MRTs already have magnetic field strengths of greater than 2 Tesla, sometimes even around 7 Tesla. These field strengths are typically generated by superconducting magnetic coils, which are current-conducting and thus magnetic even upon disconnection from the energy supply. Due to occupational safety regulations, personnel cannot be subjected to magnetic field strengths greater than 2 Tesla or comparable exposure induced by a chronological change of the magnetic flux density (for example during movement in the stray field).

For this reason, MRTs are often only cleaned at comparatively long time intervals and with great effort (among other things time expenditure), which can be problematic in hospital operation, however, for example due to hygiene requirements and/or timing of examination appointments.

SUMMARY OF THE INVENTION

The invention is based on the object of improving the cleaning of a tomography device which has an examination tunnel.

This object is achieved according to the invention by a cleaning device having the features of the first independent cleaning device claim. This object is also achieved according to the invention by a cleaning device having the features of second independent cleaning device claim. Furthermore, this object is achieved according to the invention by a tomography device having the features of the independent tomography claim. Advantageous embodiments and refinements of the invention, which are partially inventive as such, are represented in the dependent claims and the following description.

The cleaning device according to the invention is configured and provided for a tomography device having an examination tunnel, in particular an MRT. The cleaning device has for this purpose a nozzle assembly for applying a liquid cleaning agent to a tunnel inner surface facing toward the tunnel axis. Furthermore, the cleaning device has a mounting device, which is configured to mount the nozzle assembly on a structural unit of the tomography device parallel to the tunnel axis (thus an axis around which the examination tunnel extends) and displaceably along the examination tunnel.

The cleaning device is therefore configured as autonomous in that manual application of the liquid cleaning agent is not required. The cleaning device is preferably also completely autonomous, so that in particular only triggering of a cleaning procedure carried out independently by the cleaning device-expediently monitored or controlled by a control unit—is necessary.

The term "structural unit" is understood here and hereinafter in particular as a structural component which is preferably also accessible from an outside of the tomography device. For example, the structural unit is a patient table, on which a patient is pushed through the examination tunnel in the intended operation of the tomography device, or a support structure for this patient table.

"MRT" is understood here and hereinafter in particular as both a "pure" magnetic resonance tomography device and also a combination device based on the use of magnetic resonance, for example a PET-MRT or a MR-LINAC (the latter comprises a linear accelerator for radiation therapy).

The invention offers the advantage that cleaning personnel do not have to enter the examination tunnel and that, in particular due to the nozzle assembly, a comprehensive cleaning agent application is enabled with high repetition accuracy (in comparison to a manual application).

Preferably, a disinfectant or a combination of a "typical" cleaning agent (which typically contains detergent substances, for example surfactants) and a "typical" disinfectant (which is typically formed predominantly from alcohol or the like) is used as the liquid cleaning agent.

In one expedient embodiment, the mounting device preferably mounts the nozzle assembly in the intended usage state on a patient table of the tomography device in such a way that the nozzle assembly is also moved upon movement of the patient table. In other words, the nozzle assembly is fastened by means of the mounting device on the patient table in this embodiment.

In an alternative embodiment, the mounting device has a rail guide. By means of this, the nozzle assembly is displaceably guided separately in this case from the patient table in the examination tunnel.

In an expedient refinement, the mounting device has a rail slide in this case, which is coupled in the intended usage state to a guide rail of the patient table. In this case, the cleaning device, in particular the nozzle assembly in the intended usage state, is thus displaceably guided on a guide rail of the patient table. The nozzle assembly may thus be moved independently of the patient table.

In the case of the separate rail guide, the cleaning device preferably also has a drive, which effectuates the movement of the nozzle assembly along the rail guide and thus through the examination tunnel.

In an optional embodiment, the nozzle assembly is formed by a nozzle head having a plurality of nozzle openings. These are oriented in different radial directions relative to the movement axis of the nozzle head. The spray geometry induced in this way is such that the tunnel inner surface to be cleaned can be sprayed in a planar manner (i.e., at least linearly in a radial plane) in this case. The nozzle head is arranged on the tunnel axis here, for example. For example, the nozzle head has a diameter of approximately 10 cm.

In a preferred embodiment, the nozzle assembly has a mounting bracket (or also: mounting frame), on which a plurality of individual nozzles is arranged. These individual nozzles, comparably to the nozzle head, are in particular distributed along the mounting bracket and are preferably oriented in different radial directions. The above-described spray geometry is thus again formed. In the intended usage state, the individual nozzles are additionally expediently arranged at a comparatively small distance from the tunnel inner surface here.

In an expedient variant, the mounting bracket is formed as a circle or circular arc section. As a circular arc section, the mounting bracket is designed in particular for the case that the examination tunnel is flattened on its lower side and has an integrated guide structure for the patient table. In this case, preferably only the surface area of the examination tunnel not covered by the patient bed in the intended operation, which is accessible to the patient, is subjected to cleaning agent. The mounting bracket is thus preferably shaped in accordance with the inner contour (at least the area thereof accessible to the patient) of the examination tunnel in this case. This advantageously enables the individual nozzles each to be arranged at least nearly at the same distance to the tunnel inner surface.

In an alternative variant, the mounting bracket is configured as polygonal, for example as a rectangle.

In a further embodiment which is expedient or which also forms an invention alone as such, the cleaning device (therefore alternatively or optionally additionally to the nozzle assembly) has a wiper assembly. This is configured to mechanically clean the tunnel inner surface under the effect of the (liquid) cleaning agent and/or—in particular in case of the combination with the nozzle assembly—to absorb the cleaning agent again. For this purpose, the wiper assembly preferably carries a number of mechanical cleaning elements. In the case of the combination with the nozzle assembly, the wiper assembly is advantageously mounted after the nozzle assembly in an intended feed direction thereof. In other words, the wiper assembly is arranged in this case so that it follows the nozzle assembly and thus can preferably distribute, incorporate, and/or absorb the applied liquid cleaning agent again. This is advantageous in that a wiping disinfection is regularly more effective than a spraying disinfection alone.

In the above-described embodiment, which is inventive alone as such, the nozzle assembly can also not be provided in the cleaning device. The mounting device is configured in this case to mount the wiper assembly parallel to the tunnel axis and displaceably along the examination tunnel on the tomography device.

The features of the mounting device described above with reference to the nozzle assembly preferably also apply accordingly to the embodiment in which only the wiper assembly is provided.

The cleaning device preferably also has a control unit (in particular the above-mentioned control unit), which is configured to specify the movement (for example the feed speed) of the nozzle assembly and/or the wiper assembly through the examination tunnel and thus to control the cleaning procedure in the intended cleaning operation. Alternatively or additionally, the control unit is configured to specify the application of the cleaning agent in dependence on the movement of the nozzle assembly (relative to the tomography device) and/or on the movement of the wiper assembly. The "application of the cleaning agent" is to be understood in this case in particular such that it can take place both by spraying by means of the nozzle assembly and also by mechanical application, for example by means of soaked cleaning elements of the wiper assembly.

"In dependence on the movement of the nozzle assembly" is understood here and hereinafter in particular to mean that the application of the cleaning agent is specified in dependence on the position of the nozzle assembly in the examination tunnel and/or on a feed speed of the nozzle assembly during its movement through the examination tunnel. The position dependence can be advantageous, for example, in the case of an irregular surface of the tunnel inner surface, so that at some points more cleaning agent has to be applied. The speed dependence is implemented, for example, in that at a high feed speed, a comparatively higher cleaning agent flow rate is specified than at a low feed speed, in particular such that the most constant possible application per unit of area (with respect to the amount of the cleaning agent) always takes place.

In one expedient embodiment—in particular for the case that the (in particular separate) nozzle assembly is not provided—the cleaning element, preferably each of possibly several of the cleaning elements, of the wiper assembly is coupled to a cleaning agent feed, for example a line (in particular a hose or the like) discharging at the corresponding cleaning element, so that the corresponding cleaning element, in this case preferably a sponge, a brush, a cloth, or the like can be soaked (in particular automatically) using the cleaning agent for application of the cleaning agent. In principle, however, it is also possible and optionally also designed so that in the intended operation, the corresponding cleaning agent is soaked manually, preferably before the wiper assembly enters the examination tunnel.

In the preceding case, in which the corresponding cleaning element is soaked by means of the line discharging thereon, the orifice of the line is expediently configured in the form of a type of nozzle so that the cleaning element can be kept sufficiently moist to enable a continuous application of the cleaning agent to the tunnel inner surface. A type of fishtail nozzle or also a type of perlator can be selected here in order to be able to introduce the cleaning agent in the corresponding cleaning element over the largest possible area and/or for the most complete possible soaking or wetting.

The control unit is preferably formed at least in essence by a microcontroller having a processor and a data memory, in which the functionality for carrying out the cleaning procedure is implemented by programming in the form of operating software (firmware). The cleaning procedure can expediently be carried out in this case automatically upon execution of the operating software in the microcontroller-possibly in interaction with an operator. This operating software is optionally integrated in a higher-order control unit—for example of the tomography device-so that the control unit of the cleaning device is formed by the control unit of the tomography device. The control unit can also be formed in the scope of the invention by a non-programmable electronic component, for example an ASIC, in which the functionality for carrying out the cleaning procedure is implemented using circuitry means. Alternatively, an embodiment is also conceivable and provided in the scope of the invention in which the control unit is embodied mechanically, hydraulically, or pneumatically. In this case, the application of the cleaning agent expediently takes place driven by the (in particular feed) movement of the nozzle assembly or the wiper assembly, for example by means of a motion-sensing element (for example, a friction wheel, a push rod, a tappet, or the like), which is in contact with the tomography device in the intended usage state, and effectuates the delivery of the cleaning agent and/or the movement of the wiper assembly. The movement of the nozzle or wiper assembly can optionally also be carried out manually in this case (in particular by a displacement of the nozzle and/or wiper assembly in the examination tunnel) by an operator.

In one expedient embodiment, in particular for the case that the mounting device mounts the nozzle assembly or the wiper assembly in the intended usage state on a patient table of the tomography device, the control unit is integrated into the (in particular higher-order) control unit of the tomography device.

Furthermore, the optionally provided drive of the rail guide assigned to the cleaning device is expediently linked with respect to control to the control unit.

The distance (in the feed direction) between the nozzle assembly and the wiper assembly is optionally selected here so that at a predetermined feed speed, a sufficiently long action time of the liquid cleaning agent is provided. Additionally or alternatively, the control unit is designed and configured to specify the feed speed differently in dependence on the distance and a recommended action time-which is often dependent on the type of the cleaning agent used.

The wiper assembly is preferably a second (for example round or polygonal) mounting bracket, which is in particular guided jointly with the nozzle assembly. Sponges, cloths, brushes, and/or leveling lips (also referred to colloquially as "rubber lips") are in turn arranged thereon as cleaning elements, which are suitable for distributing or absorbing the cleaning agent, in particular for wiping disinfection. In an optional variant, sponges, cloths, or brushes—possibly coupled to the above-described cleaning agent feed—are arranged here in front of the leveling lips (or optionally also only one leveling lip shaped in accordance with the contour of the tunnel inner surface) in the feed (or also: insertion) direction.

In a further optional embodiment of the nozzle assembly—which can also be used if the wiper assembly is provided—it is not designed, as described above, for the spray application of the cleaning agent, but rather for "mechanical" application, comparably to the above-described variant of the wiper assembly. For this purpose, the nozzle assembly comprises one application element or optionally multiple application elements, which is or are interconnected between the nozzles of the nozzle assembly and the tunnel inner surface. The respective application element is, for example, a sponge body or the like. In the intended operation, it is soaked using the cleaning agent "on the rear" by means of the respective nozzle and can apply this cleaning agent to the tunnel inner surface by touching it on the front. In this case, the respective nozzle of the nozzle assembly is thus configured to transfer the cleaning agent to the application element. In contrast, in the case of the above-described spray application, the respective nozzle is configured so that the above-described spray geometry is achieved on the tunnel inner surface.

In one expedient refinement, the wiper assembly has a drive for movement, decoupled from the nozzle assembly, of the cleaning elements acting mechanically on the tunnel inner surface. For example, this drive contains an electric motor. Alternatively, the drive is formed by a gearing, a link guide, or the like, which interacts, for example, with the above-described rail guide (or a partial surface of the cleaning tunnel, for example by means of a friction wheel) in such a way that the cleaning elements are moved transversely to the feed movement during a feed movement.

In one advantageous embodiment, the cleaning device comprises a storage container and possibly also a collection container for the cleaning agent. In the intended cleaning operation, this is or these are preferably arranged outside the examination tunnel. For this purpose, the cleaning device comprises corresponding connecting means, in particular an assigned hose, for example, to connect the storage container to the nozzle assembly.

For the case that a collection container is provided, a collection channel or the like is expediently arranged on the wiper assembly, into which the cleaning agent running off of leveling lips can run in particular and can flow therefrom to the collection container. A suction device is optionally also provided in this case, which can "suck up" the cleaning agent.

In one particularly preferred embodiment, elements of the cleaning device which enter the examination tunnel in the intended cleaning operation are formed with the omission or at least reduction of magnetic, in particular ferromagnetic material. In particular, such elements are the nozzle assembly, the possibly provided wiper assembly, the mounting device, and possibly provided lines for the cleaning agent. It is thus advantageously possible to prevent these elements from being attracted by the magnetic coils used therein during the use of the cleaning device in an MRT. The cleaning of the MRT can thus be carried out while observing the safety guidelines without the presence of personnel in the vicinity of the MRT.

In an optional embodiment, the cleaning device-additionally or alternatively to the wiper assembly—has a UV radiator assembly for UV irradiation (for disinfection purposes) of the tunnel inner surface.

The tomography device according to the invention is preferably configured as an MRT. The tomography device has an examination tunnel and the above-described cleaning device. The tomography device therefore has the same features and thus also the same advantages as the cleaning device.

The conjunction "and/or" is to be understood here and hereinafter in particular in such a way that the features linked by means of this conjunction can be formed both jointly and also as alternatives to one another.

Other features which are considered as characteristic for the invention are set forth in the appended claims.

Although the invention is illustrated and described herein as embodied in a cleaning device for a tomography device having an examination tunnel and tomography device, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DETAILED DESCRIPTION OF THE INVENTION

Parts corresponding to one another are always provided with the same reference signs in all figures.

Figure 1:
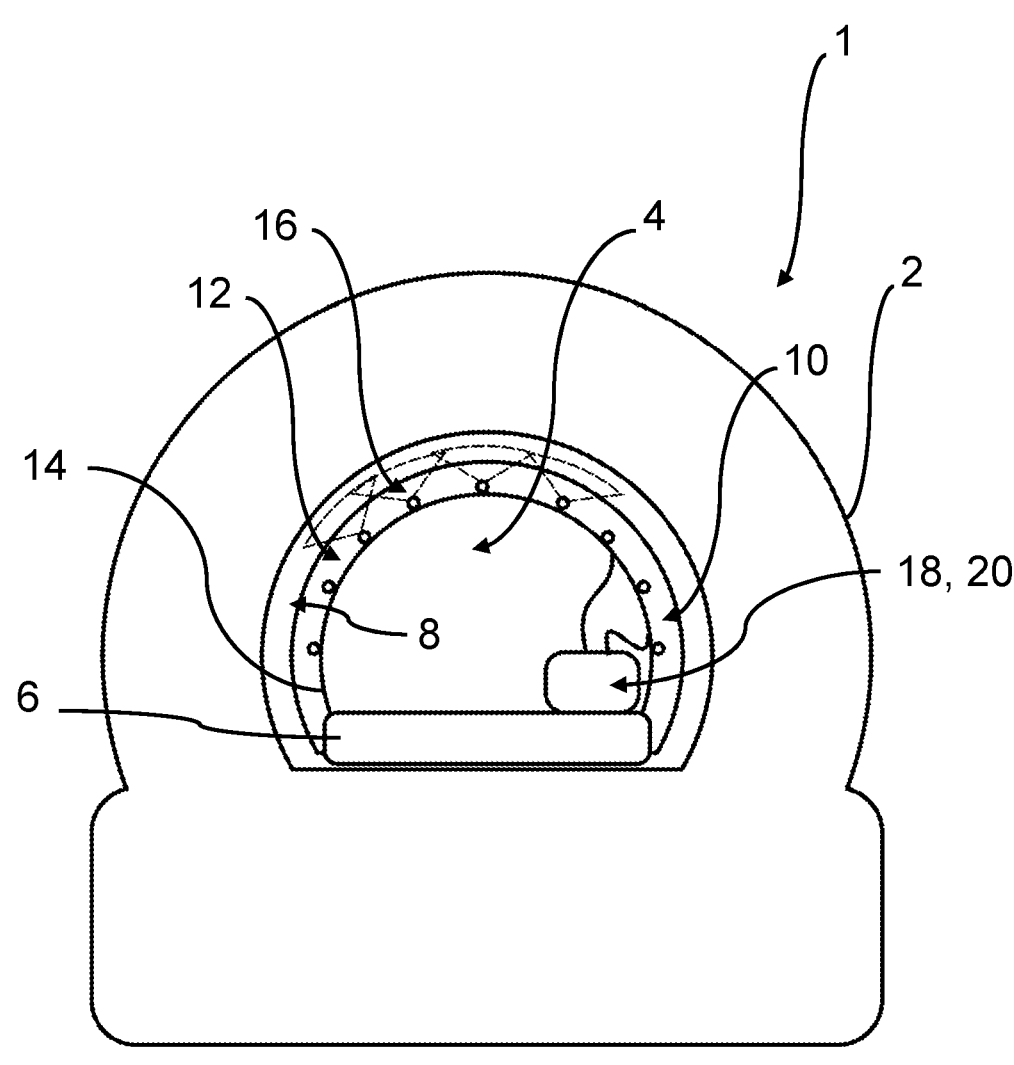
FIG. 1 is a schematic view of a tomography device having a cleaning device.

Referring now to the figures of the drawings in detail and first, particularly to FIG. 1 thereof, there is shown a tomography device, specifically a magnetic resonance tomography device, abbreviated "MRT 1". The MRT 1 has a housing 2, in which annular magnetic coils are arranged, so that an examination tunnel, abbreviated "tunnel 4", is formed in the center thereof. A patient is moved by means of a patient table 6 guided on the housing 2 through this tunnel 4 in the intended examination operation.

A part of a tunnel inner surface 8 bounding the tunnel 4 is accessible here to the patient lying on the patient table 6. For this reason, it is expedient to clean, in particular to disinfect, this part of the tunnel inner surface 8 regularly. It is problematic here—as can be seen in particular from FIG. 3—that in MRTs the tunnel 4 is usually comparatively long, often longer than 1.5 m at a tunnel diameter of approximately 60 to 70 cm. The accessibility for cleaning is thus already made more difficult. In addition, in modern MRTs, the magnetic field strength—also in the inactive state due to superconducting materials—is usually above the permissible workplace load of 2 Tesla, so that cleaning by cleaning personnel is only possible with difficulty.

For this reason, a cleaning device 10 is assigned to the MRT 1. This has a nozzle assembly 12, which is configured to dispense a liquid cleaning agent, especially a disinfectant specifically, onto the tunnel inner surface 8. For this purpose, the nozzle assembly 12 contains a mounting bracket 14, on which multiple spray nozzles 16 (also: "individual nozzles") are arranged in such a way that the tunnel inner surface 8 to be sprayed, specifically the part thereof to be disinfected, can be sprayed in a planar closed manner. For this purpose, the spray nozzles 16 are each aligned in different radial directions relative to a tunnel axis of the tunnel 4 or the displacement axis of the patient table 6. The mounting bracket 14 is configured in the present exemplary embodiment as a circular arc section, so that all spray nozzles 16 (at least approximately) have the same distance to the tunnel inner surface 8. The cleaning device 10 also has a mounting device (not shown in greater detail here), by means of which the mounting bracket 14 of the nozzle assembly 12 is fixed on the patient table 6, specifically at its end (see FIG. 3). The cleaning device 10, at least the nozzle assembly 12, can thus be moved through the tunnel 4 by moving the patient table 6. An additional drive is therefore not necessary.

Furthermore, the cleaning device 10 has a control unit 18, which is shown as a "black box" on the patient table 6 in the present exemplary embodiment. However, the control unit 18 is preferably integrated as a software component in a control unit of the MRT 1. A storage container 20 for the cleaning agent is also contained in the "black box" shown. The control unit 18 is configured to control the dispensing of the cleaning agent in dependence on the axial position of the patient table 6 and thus the nozzle assembly 12 and/or on the feed speed of the patient table 6.

In one embodiment (not shown in greater detail), the storage container 20 and an expediently assigned pump are also arranged outside the tunnel 4, for example adjacent to the housing 2, and are coupled using a connecting line to the spray nozzles 16.

In a simple embodiment of the cleaning device 10, only a spraying disinfection of the tunnel inner surface 8 is carried out.

In order that the parts of the cleaning device 10 are not attracted (or displaced in general terms) by the magnetic field of the magnetic coils, the parts of the cleaning device 10, specifically the elements which enter the tunnel 4 during the cleaning procedure, are formed from a non-ferromagnetic material.

Figures 2, 3:
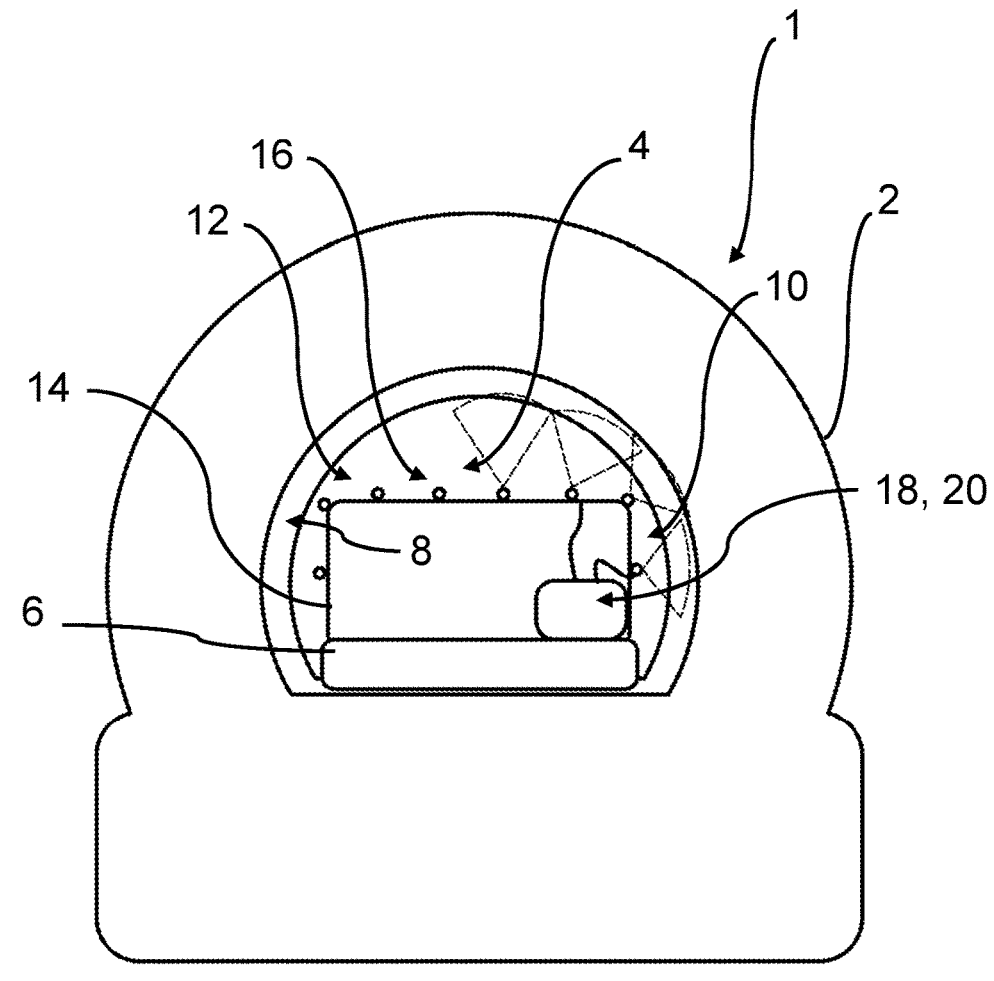
FIG. 2 is a schematic view according to FIG. 1 of a further exemplary embodiment of the cleaning device.
FIG. 3 is a schematic side view of a patient table having a further exemplary embodiment of the cleaning device.

An alternative exemplary embodiment of the cleaning device 10 is shown in FIG. 2. The mounting bracket 14 is configured to be approximately rectangular in this case. Otherwise, the structure corresponds to the cleaning device 10 according to FIG. 1.

A further exemplary embodiment of the cleaning device 10 is schematically shown in FIG. 3. This contains a wiper assembly 22 here in addition to the nozzle assembly 12. This is arranged trailing the nozzle assembly 12 in a feed direction 24. In other words, the nozzle assembly 12 is introduced first into the tunnel 4 during the entry of the patient table 6 into the latter. The wiper assembly 12 has, in addition to a mounting bracket 26, multiple cleaning elements mounted on the latter, in the form of sponges 28 here. These are either arranged so that a closed contact line or surface is formed over the part of the tunnel inner surface 8 to be cleaned. Alternatively, the sponges are moved (for example rotated) by means of a drive (not shown in greater detail) in such a way that a planar closed wiping of this part of the tunnel inner surface 8 is enabled.

Upon the entry into the tunnel 4, the tunnel inner surface 8 is thus initially sprayed linearly transversely to the feed direction 24 by means of the spray nozzles 16 and thus in a planar manner due to the feed. After sufficient action time of the cleaning agent, the latter is subsequently wiped off by means of the sponges 28. The action time results here from the feed speed of the patient table 6 and the distance between nozzle assembly 12 and wiper assembly 22.

In addition to the storage container 20, a collection container 30 is also provided here, in which cleaning agent absorbed by means of the sponges 28 is accommodated. For example, the sponges 28 are connected for this purpose to a suction device.

In an alternative exemplary embodiment (not shown in greater detail), only the wiper assembly 22 is provided in place of the nozzle assembly 12. In this case, the supply of the cleaning agent takes place into the sponges 28, by means of which the application of the cleaning agent thus takes place. In this case, the suction device can also be omitted and drying can take place in the air. Otherwise, the features described on the basis of FIGS. 1 and 2 also apply, transferred accordingly, to the wiper assembly 22.

The subject matter of the invention is not restricted to the above-described exemplary embodiments. Rather, further embodiments of the invention can be derived by a person skilled in the art from the above description. In particular, the individual features of the invention described on the basis of the various exemplary embodiments and the design variants thereof can also be combined with one another in another way.

The following is a summary list of reference numerals and the corresponding structure used in the above description of the invention.

LIST OF REFERENCE NUMERALS

1 MRT
2 housing
4 tunnel
6 patient table
8 tunnel inner wall
10 cleaning device
12 nozzle assembly
14 mounting bracket
16 spray nozzle
18 control unit
20 storage container
22 wiper assembly
24 feed direction
26 mounting bracket
28 sponge
30 collection container

The invention claimed is:

1. A cleaning device for a tomography device having an examination tunnel, the cleaning device comprising:
  a wiper assembly configured to clean a tunnel inner surface facing toward a tunnel axis mechanically under an effect of a liquid cleaning agent; and
  a mounting device configured to mount said wiper assembly on a structural unit of the tomography device parallel to the tunnel axis and displaceably along the examination tunnel.

2. The cleaning device according to claim 1, wherein:
  the structural unit of the tomography device is a patient table; and
  said mounting device is configured to mount said wiper assembly in an intended usage state on the patient table of the tomography device, so that said wiper assembly is also moved upon movement of the patient table.

3. The cleaning device according to claim 1, wherein said mounting device has a rail guide, by means of which said wiper assembly is displaceably guided separately from a patient table in the examination tunnel.

4. The cleaning device according to claim 3, wherein said mounting device has a rail slide, which is coupled in an intended usage state to a guide rail of the patient table.

5. The cleaning device according to claim 1, further comprising:
  moving cleaning elements acting mechanically on the tunnel inner surface; and
  a drive for moving said moving cleaning elements acting mechanically on the tunnel inner surface.

6. The cleaning device according to claim 1, wherein elements of the cleaning device entering the examination tunnel in an intended cleaning operation are formed with omission or at least reduction of ferromagnetic material.

7. The cleaning device according to claim 1, further comprising an ultra-violet (UV) radiator assembly for UV irradiation of the tunnel inner surface.

\* \* \* \* \*